United States Patent
Seeman

(10) Patent No.: US 11,468,039 B2
(45) Date of Patent: Oct. 11, 2022

(54) SECURE COMPUTER PERSONALIZATION

(71) Applicant: Lisa Seeman, Beit Shemesh (IL)

(72) Inventor: Lisa Seeman, Beit Shemesh (IL)

( * ) Notice: Subject to any disclaimer, the term of this patent is extended or adjusted under 35 U.S.C. 154(b) by 416 days.

(21) Appl. No.: 16/603,320

(22) PCT Filed: Apr. 5, 2018

(86) PCT No.: PCT/IB2018/052351
§ 371 (c)(1),
(2) Date: Oct. 7, 2019

(87) PCT Pub. No.: WO2018/185692
PCT Pub. Date: Oct. 11, 2018

(65) Prior Publication Data
US 2021/0279228 A1    Sep. 9, 2021

Related U.S. Application Data

(60) Provisional application No. 62/482,213, filed on Apr. 6, 2017.

(51) Int. Cl.
*G06F 16/23*    (2019.01)
*G06Q 40/00*   (2012.01)

(52) U.S. Cl.
CPC ......... *G06F 16/2365* (2019.01); *G06Q 40/12* (2013.12)

(58) Field of Classification Search
CPC ............ G06F 16/2365; G06F 16/3011; G06F 16/335; G06F 16/9035
USPC ....................................................... 707/803
See application file for complete search history.

(56) References Cited

U.S. PATENT DOCUMENTS

| 7,554,522 | B2* | 6/2009 | Sinclair, II | G06F 3/0481 |
| | | | | 706/11 |
| 2002/0095292 | A1* | 7/2002 | Mittal | G10L 21/06 |
| | | | | 704/E21.019 |
| 2002/0138616 | A1* | 9/2002 | Basson | G06Q 20/123 |
| | | | | 709/225 |
| 2003/0061317 | A1* | 3/2003 | Brown | G06F 16/9577 |
| | | | | 709/221 |
| 2004/0128389 | A1* | 7/2004 | Kopchik | G06F 21/34 |
| | | | | 709/228 |
| 2006/0004607 | A1* | 1/2006 | Marshall | G16H 40/67 |
| | | | | 707/E17.09 |

(Continued)

*Primary Examiner* — James Trujillo
*Assistant Examiner* — Fariborz Khoshnoodi
(74) *Attorney, Agent, or Firm* — The Law Office of Joseph L. Felber

(57) ABSTRACT

Embodiments disclosed herein include methods and apparatuses for providing security to computer users with disabilities, who configure their computers to personalize output in a fashion that enables the user to more easily understand the content of the output. While previously a computer configured to personalize output accordingly may have served as a source of disability information to unauthorized parties accessing the computers, embodiments disclosed herein configure computers for personalization without leaving thereon a record how the personalization was specified during the configuration process. Thus, an unauthorized party gaining access to the user's computer would find it very difficult, if not impossible, to determine the user's disability from an inspection of the computer, so the user is much less likely to become a victim of fraud based on an unauthorized discovery of information regarding vulnerabilities.

9 Claims, 6 Drawing Sheets

(56) References Cited

U.S. PATENT DOCUMENTS

| | | | |
|---|---|---|---|
| 2007/0055938 A1* | 3/2007 | Herring | G06F 16/9577 |
| | | | 715/729 |
| 2010/0121928 A1* | 5/2010 | Leonard | H04L 63/1433 |
| | | | 709/206 |
| 2010/0188230 A1* | 7/2010 | Lindsay | G16H 40/63 |
| | | | 715/866 |
| 2011/0154212 A1* | 6/2011 | Gharpure | G09B 21/00 |
| | | | 709/219 |
| 2013/0145457 A1* | 6/2013 | Papakipos | G06F 21/6245 |
| | | | 726/19 |
| 2016/0292404 A1* | 10/2016 | Tseng | G06F 21/6245 |
| 2019/0378225 A1* | 12/2019 | Kundu | H04L 65/611 |

* cited by examiner

Specify Settings

Select Template Name: Seeing Impaired

This profile template is designed to aid the seeing impaired

On this page you can edit it to fit your own personal state:

- Profile Name: [My Profile]
- Contrast Level: [High Contrast ▼] — 70
- Text Sizes: [Very Large ▼] — 72
- Provide personal explanation to: [Homepage link ▼] — 74
- How personal explanations are shown: [As Tooltip ▼] — 76

[Manually edit the profile file (Not recommended for beginners)] — 78

[Save Changes] — 80

FIG. 4C

You are about to spend $800 at a supermarket, which greatly exceeds your budget (100%).

Do you wish to continue with this sale?

| Yes - I want to spend more that my budget now. | No - Cancel this deal. I can make a new deal with fewer items. |

- I need time to think. Ask me in an hour.
- This does not make sense! I need to speak to someone.

Provide fingerprint confirmation

FIG. 5

SECURE COMPUTER PERSONALIZATION

RELATED APPLICATION

This application claims benefit under 35 U.S.C. § 119(e) of the Apr. 6, 2017 filing of U.S. Provisional Application No. 62/482,213, which is hereby incorporated by reference in its entirety.

BACKGROUND

Persons with disability meet obstacles often unnoticed by others. This phenomenon extends to the realm of computer output interfaces. While the general population may enjoy advances in output technologies, such as flashing text, graphics, a wide array of colors, contrasting brightnesses, and special sounds, such variety in outputs can be problematic to persons with certain disabilities. Accordingly, output properties are often modified, that is, personalized, for individual users to accommodate their disabilities.

Many types of personalization are available to display output so that it is appropriate for the particular disability a user has. For example, a person with photophobia, an extreme sensitivity to light, may want computer output to display without flashing and bright lights, with low contrast, and without moving content. Another person, having low vision, that is, a visual impairment that cannot fully be corrected by corrective lenses or surgery, may want high contrast and magnified content. The person with low version may also want linearized content, that is, a one-column design instead of a multiple-column or table-type design.

Some persons have temporary disabilities. An example is a parent, who usually has no trouble with an unmodified computer display, but when her child needs emergency medical attention becomes highly stressed to the point that she cannot effectively use a computer that is not personalized for her temporary condition. The personalization appropriate for her may be a reduction in lower priority content, which provides unnecessary distractions. For example, when searching her medical care provider's web site for the immediate action to take after her child ingests a poisonous substance, she will not want to see links and windows opening to offer her upgrades to service plans or articles to tell her how to prepare for seasonal climate changes as they affect health. A personalization to remove these distractions enables her to more quickly find the information she needs immediately. Once the personalization is set up on the user's computer, she can manually activate the personalization as needed by simple means, such as by clicking on a prominent button, or software installed on the user's computer may automatically detect the stressed condition, such as, by observing an increased frequency of misspelled words or other data entry abnormalities. With the automatic detection in place, the system swiftly transitions to the emergency mode without requiring specific user input.

One way to personalize a client computer, which obtains Internet content using a browser, is to install on the browser an extension personalized for the disability that the user has. Such is only one non-limiting example of personalization, as personalization can be provided for content not arriving via a browser and/or from the Internet. Note is made also that, despite potential differing nuances of the terms "extension," "plugins," "add-ons," and similar terms in the present context, this disclosure refers to the terms synonymously.

With the advantages of personalization also come the disadvantages. The user with the personalized computer has increased exposure to fraud, that is, fraud that is directed more to persons without disabilities. For example, a malevolent party knowledgeable that a user has low vision may attempt to evade the personalization and find a way to offer deals to the user by presenting a deal's objectional clauses and conditions in lower contrast and in smaller font. In another example, a user temporarily disabled due to a high level of stress may hear/read a vendor offer "two for the price of three" and accept the offer as if the vendor really offered "three for the price of two."

Therefore, having a personalized computer becomes a security risk, when an inspection of the computer can indicate to a malevolent party the disability that the user has. The disability may be readily apparent, for example, if it is seen that the browser has installed thereon an extension named "Photophobia Corrector." Indication of the disability may instead be less apparent, but a malevolent party with a suitable background in software may still be able to detect the disability.

Accordingly, a computer stolen from a residence, personal vehicle, public transportation, or other public area, may expose a user to more attempted fraud, after the user's disability is discovered. Further, the risks are not limited to the physical theft of the computer. Malware unknowingly loaded onto a user's computer may be capable of discovering the details of personalization and the associated disability and then reporting the finding to a malevolent party.

Accordingly, there exists a need for a way to personalize a computer for a user with disabilities in such a way that unauthorized parties would find it very difficult, if not impossible, to determine the user's disability from an inspection of the computer.

SUMMARY

Embodiments of the present invention guard against fraud by increasing the difficulty malevolent parties would have trying to find the vulnerabilities of computer users. The invention may be embodied as a personalized client computer, as a server computer providing the personalization, or as a method of personalizing a client computer, as non-limiting examples.

More specifically, the invention may be embodied as a client computer for a user with a disability. The client computer has a processor and a memory. The memory stores instructions that, when executed, causes the processor to personalize content based on a personalization file, received through a network, to accommodate the disability. The personalization file does not identify input personalization data that was used to generate the personalization file, and this reduces the ability to identify the user's disability from the personalization file.

The invention may also be embodied as a personalization service server computer for enabling a client computer to personalize content for a user with a disability. The server computer has a personalization engine. When the personalization engine is activated, it: accepts through a network data that specifies the personalization to accommodate the user having a particular disability; generates a personalization file based on the received data; and provides through the network the personalization file to the client computer. The client computer uses the personalization file to personalize content to accommodate the user.

The invention may further be embodied as a method of enabling a client computer to personalize content for a user with a disability. The method includes: receiving through a network data that specifies the personalization to accommodate the user having a particular disability; generating a personalization file based on the received data; and providing through the network the personalization file to the client computer. The client computer uses the personalization file to personalize content to accommodate the user.

The invention may additionally be embodied as a method of enabling a client computer to personalize content for a user with a disability. The method includes: receiving first data that specifies the personalization to accommodate the user having a particular disability; generating a first personalization file based on the first data; and providing the first personalization file to the client computer. The client computer uses the first personalization file to personalize content to accommodate the user. Also, the first data is stored securely and made available so that a second personalization file can be generated based both on the first data and on second data that specifies additional personalization to accommodate time-varying user skills and/or abilities.

In each of the embodiments summarized above, the client computer is personalized in such a way that an unauthorized party gaining access thereto would find it very difficult to determine the user's disability from an inspection of the client computer. Accordingly, the user is less likely to become a victim of fraud.

Embodiments of the present invention are described in detail below with reference to the accompanying drawings, which are briefly described as follows:

BRIEF DESCRIPTION OF THE DRAWINGS

The invention is described below in the appended claims, which are read in view of the accompanying description including the following drawings, wherein:

FIGS. 4A-4C illustrate screenshots of web pages of a user interface for implementing an embodiment of the invention; and FIG. 5 illustrates a notification provided by an application according to another embodiment of the invention.

DETAILED DESCRIPTION

Figure 1:
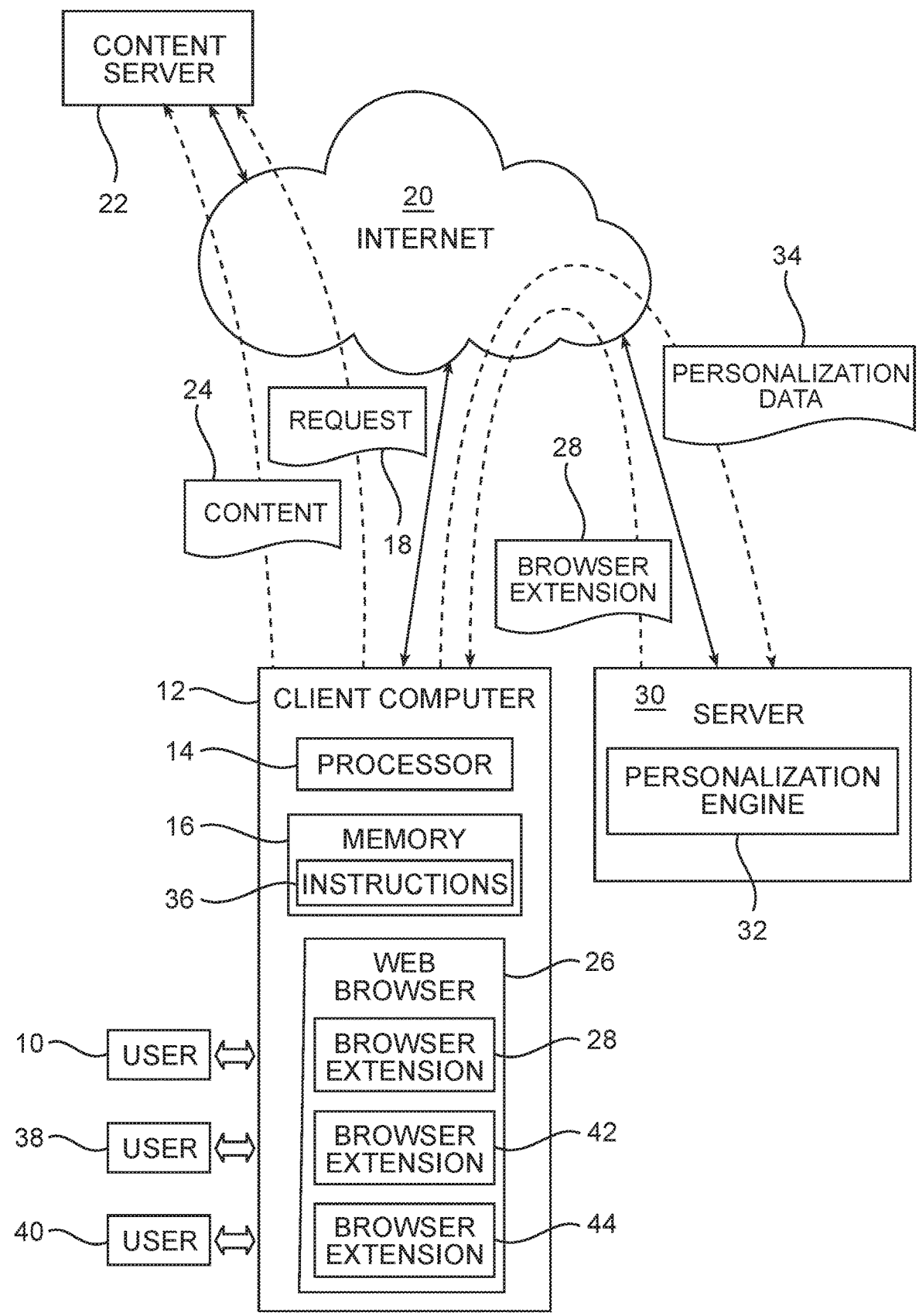
FIG. 1 illustrates a system implementing various aspects of the invention.

The invention summarized above and defined by the claims below will be better understood by referring to the present detailed description of embodiments of the invention. This description is not intended to limit the scope of claims but instead to provide non-limiting examples of the invention.

A system implementing various aspects of the invention is described as follows with reference to FIG. 1.

To access desired content, a user 10 operates a client computer 12, which in this embodiment is a personal computer (PC). In alternate embodiments the client computer can be a workstation, tablet, personal digital assistant (PDA), or smartphone, as non-limiting alternative example embodiments. The client computer 12 has a processor 14 and a memory 16.

The client computer 12 sends a request 18 for content through the Internet 20 to a content server 22, which may be a news site or customer support site, as non-limiting examples, and the content requested may be news reports or product information, respectively. The content server 22 responds to the user's request 18 by sending the requested content 24 through the Internet 20 to the client computer 12. In this implementation, the content server 22 maintains a website for the convenience of users requesting content, and the user 10 visits the website using a web browser 26 residing on the client computer 12.

The client computer 12 personalizes the content 24 from the content server 22 to accommodate the user 10 in view of his disability. In this embodiment, a specially-scripted extension 28 installed on the browser 26 enables the client computer 12 to personalize the content for the user 10. For security, the extension 28 is incorporated in such a fashion (discussed below) to increase the difficulty that an unauthorized party, given access to the client computer 12, would have attempting to determine whether the user 10 has a disability and, if so, which disability it may be.

To obtain the specially-scripted extension 28 to personalize the client computer 12, the user 10 instructs the client computer 12 to begin communication through the Internet 20 with a personalization service provided by a server 30. The personalization service server 30 has a personalization engine 32 residing thereon.

When activated by a request for personalization, such as from the client computer 12, the personalization engine 32 accepts through the Internet 20 data 34 that specifies the personalization desired to accommodate the user 10 in view of his particular disability. The data 34 may specify the disability, such as low vision or photophobia, and/or the particularly desired accommodation, such as a high or low contrast display of output. The user 10 or another party, such as a caretaker or relative of the user 10, may enter the personalization data 34 via a series of web pages provided by the personalization service server 30, or the personalization data 34 may be provided by sending a single file to the personalization service server 30, as non-limiting examples. In this embodiment, the personalization data 34 comes from the client computer 12. However, in alternate embodiments the personalization data 34 may be sent to the personalization service server 30 from a different source, for example, from a different client computer, one that is operated by a caretaker or relative of the user.

Based on the received personalization data 34, the personalization engine 32 generates an extension 28 for the web browser 26 of the client computer 12. The extension 28 is one type of personalization file a personalization engine may generate in accordance with embodiments of the present invention. In other implementations, the personalization file may be another type of personal executable script instead of a browser extension. In still further implementations, the personalization file may be an encrypted profile file to be used by an extension that is already installed on the browser of a user's client computer.

After the personalization engine 32 generates the extension 28, the personalization service server 30 provides the extension 28 through the Internet 20 to the client computer 12, where it is installed on the browser 26. Accordingly, instructions 36 stored in the memory 16 of the client computer 12, when executed, cause the processor 14 to personalize content 24 from the content server 22 based on the personalization file, that is, using the extension 28, to accommodate the user's disability. In the alternate embodiment in which the personalization file is instead an encrypted profile file, the instructions stored in the memory would configure the browser to use the profile file to personalize the content for the user. Note that in the present context "instructions" is a broad term that can include elements of the browser 26.

In some implementations, the client computer 12 may be personalized to accommodate multiple users, each desiring a different personalization. For example, the client computer 12 may be implemented as a personal computer running Windows 10 and be configured with separate accounts for users 12, 38, and 40, each user obtaining his/her own browser extension 28, 42, and 44, respectively.

The client computer 12 is personalized in such a way that an unauthorized party gaining access thereto would find it very difficult to determine the user's disability from an inspection of the client computer 12. Accordingly, the user 10 is less likely to become a victim of fraud. In the system of FIG. 1, the personalized browser extension 28 does not identify the input personalization data 34 that was used to generate it, and that reduces the ability for an unauthorized party to identify the user's disability. The client computer 12 has no direct mapping between the personalization data 34 that specified the personalization to the personalization service server 30 and the extension 28. Here, the personalization data 34 is not stored on the client computer 12 after the extension 28 is provided, so that information is not available to an unauthorized party.

The invention may also be embodied as a method of enabling a client computer to personalize content for a user with a disability. Such method is described herein with reference to the flowchart in FIG. 2. By building and maintaining a personalization engine, such as the personalization engine 32 residing on the personalization service server 30 in FIG. 1, but not limited thereto, one may perform the method as follows:

The personalization engine receives through a network data that specifies the personalization desired to accommodate the user having a particular disability. (Step S1.) In the embodiment of FIG. 1, the network is the Internet, but the network may instead be a LAN, WAN, or intranet, as non-limiting alternate examples. An example of a usage of the present method in which the network is a LAN or intranet would be that of a corporation maintaining its own personalization engine for its employees with disabilities. The user, or a caretaker, relative, or even co-worker of the user, may send the personalization data from the client computer, or alternatively the personalization data may be sent from a different source, for example, from a different client computer operated by the caretaker, relative, co-worker. Accordingly, one may assist the user from a location remote from the user.

After receiving the personalization data, the personalization engine generates a personalization file based on the received data. (Step S2.) As in the implementation of the previously-described embodiment, the personalization file may be personal executable script, such as an extension for a user's browser, or alternatively an encrypted profile file to be used by an extension that is already installed on the browser of a user's client computer, as non-limiting examples.

After the personalization file is generated, the personalization service provides through the network the personalization file to the client computer. (Step S3.) Accordingly, the client computer can use the personalization file to personalize the content it receives from a content server. If the personalization file is implemented as an extension for a client computer's browser, or as an encrypted profile file used by an extension installed already on the browser, the content to be personalized is accessed by the browser.

As in the previous embodiment, implementation of the present method effects personalization in such a way that an unauthorized party gaining access to the client computer would find it very difficult to determine the user's disability from an inspection thereof, and thus the user is less likely to become a victim of fraud. The client computer has no direct mapping between the data that specified the personalization and the personalization file. Although the data that specified the personalization may have been, but not necessarily was, stored on the client computer before the personalization engine generated the personalization file, in the present implementation, the data that specified the personalization is not stored on the client computer after the personalization file is provided thereto. Thus, the personalization data is unavailable to a party gaining unauthorized access to the client computer.

As a variation of the last embodiment described above, the method may include features to accommodate users, such as those with autism, who have varying skills and abilities at different times. The alternate method may be further modified for execution without requiring access through a network to a personalization service on a server. The method may, but is not required thereto, be performed on a client computer, such as that illustrated in FIG. 3, which has a personalization engine 46 resident thereon.

Figure 2:
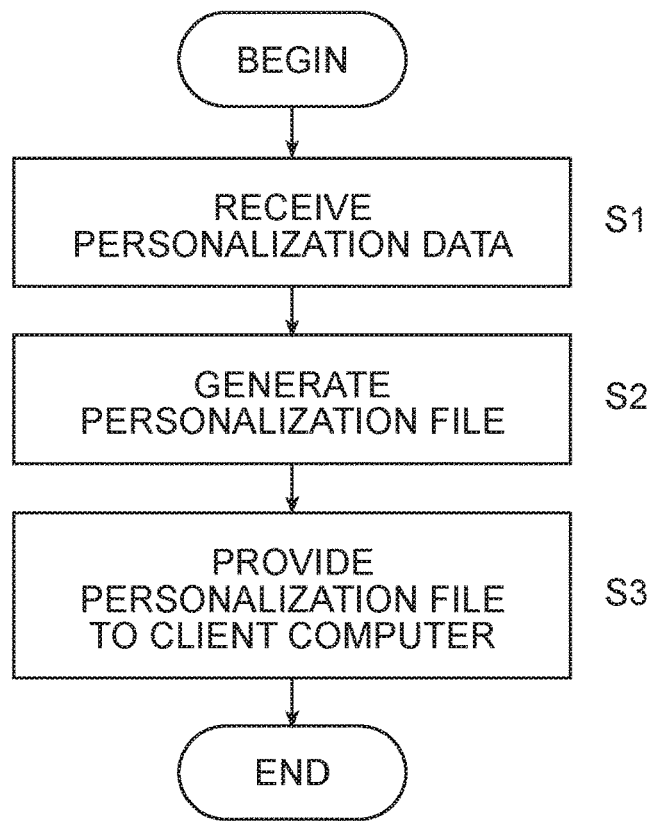
FIG. 2 provides a flowchart representing a method of enabling a client computer to personalize content for a user with a disability in accordance with embodiments of the invention.
Figure 3:
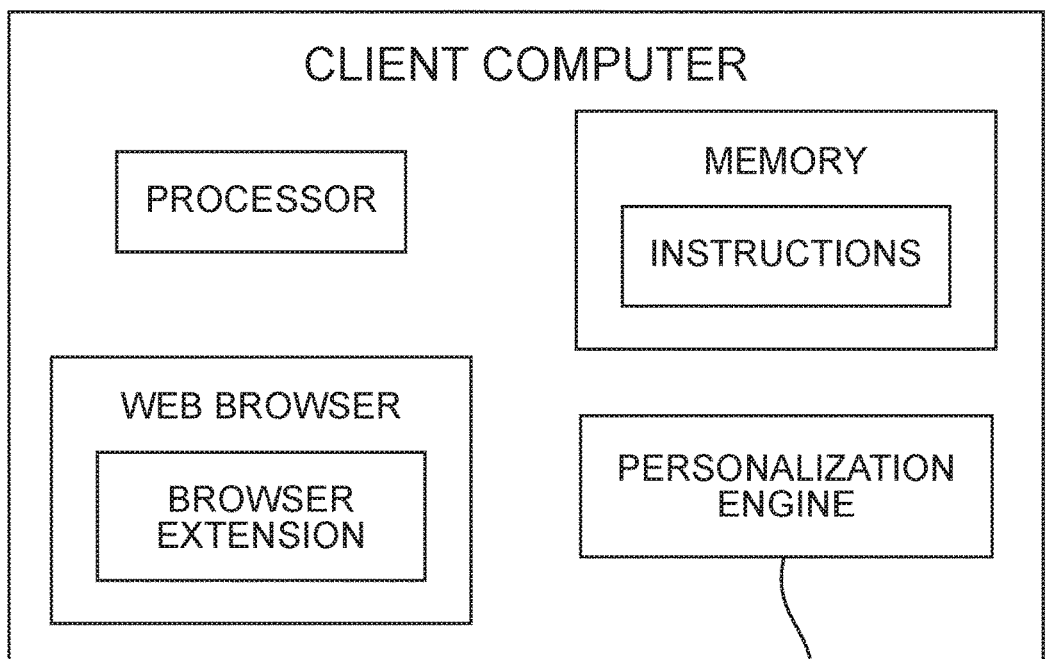
FIG. 3 provides a block diagram of a client computer in accordance with an alternate embodiment of the invention.

The personalization engine, whether residing on a server separate from the client computer, as shown for example in FIG. 1, or residing on the client computer, as shown in FIG. 3, receives data that specifies the personalization to accommodate the user having a particular disability. This data will be referenced as "first data" for this embodiment. After receiving the first data, the personalization engine generates a first personalization file based on that first data. After the first personalization file is generated, the personalization engine provides the first personalization file to the client computer. If the personalization engine resides on a server, the personalization engine sends the first personalization file through a network to the client computer. If the personalization engine resides within the client computer, the personalization engine sends the first personalization file internally. Accordingly, the client computer can use the first personalization file to personalize content to accommodate the user.

The first data is stored securely and is optionally encrypted, whether on the client computer or on a server, if the personalization engine resides on a server, and this first data is made available so that a second personalization file can be generated based both on the first data and also on additional data that shall be referenced as "second data" in this embodiment. This second data specifies which additional personalization is desired to accommodate time-varying user skills and/or abilities that the user may have.

An example user interface for implementing an embodiment of the invention is now discussed with reference to FIGS. 4A-4C. These figures illustrate screenshots of web pages that appear on a browser, such as that residing on a disabled user's client computer or on another computer operated by someone requesting a personalization file for the disabled user's browser.

Figure 4A:
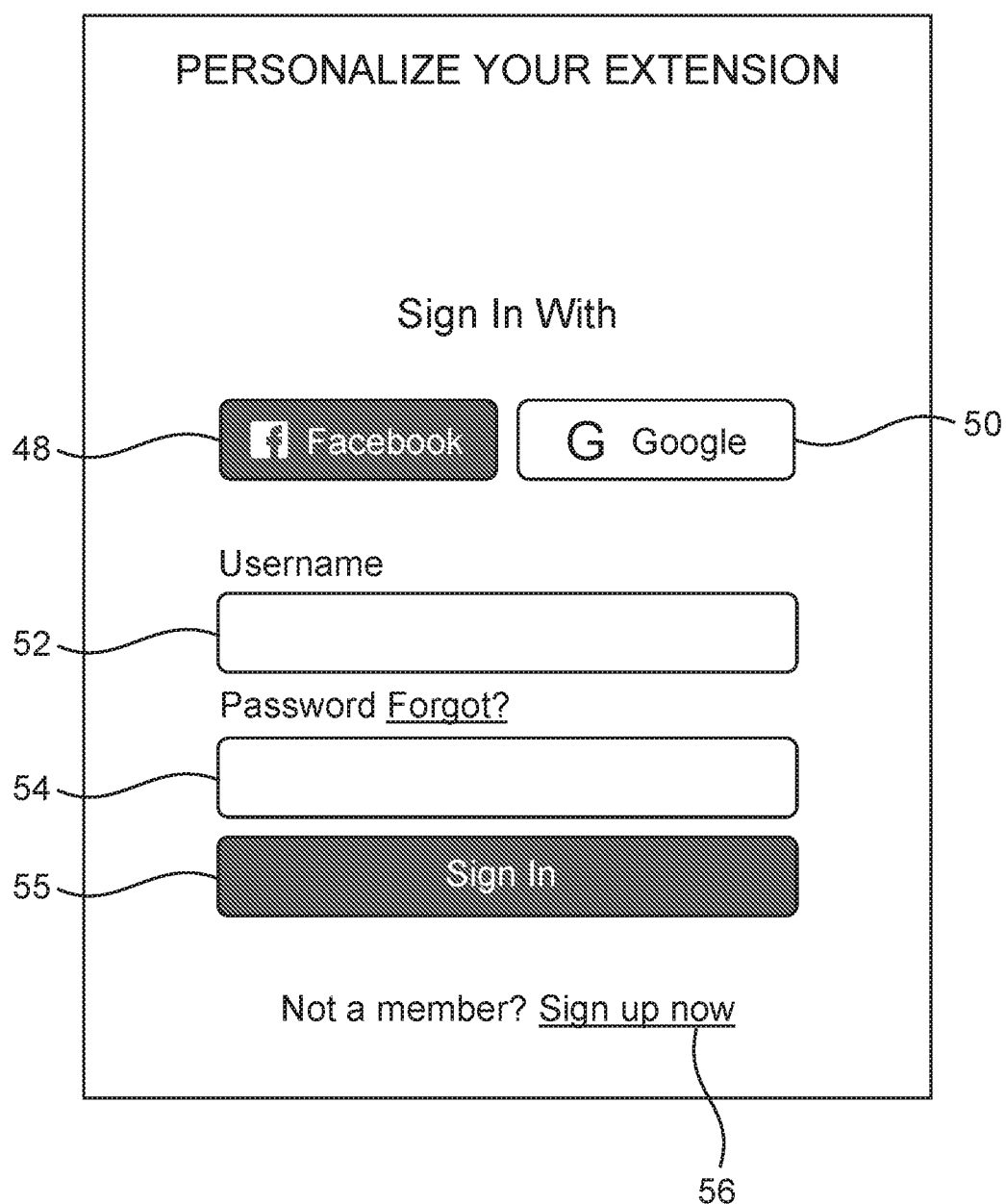

A visitor to a website maintained by a personalization service server in accordance with embodiments of the present invention initially sees in this example the web page illustrated in FIG. 4A. A visitor having an account already with the personalization service can sign in to a session using a Facebook or Google account by selecting buttons 48 or 50, respectively. Alternatively, the visitor may enter a username in field 52 and a password in field 54 and then select the "Sign In" button 55. If the visitor does not already have an account with the personalization service, he may establish an account by selecting the link labeled "Sign up now" 56.

Figure 4B:
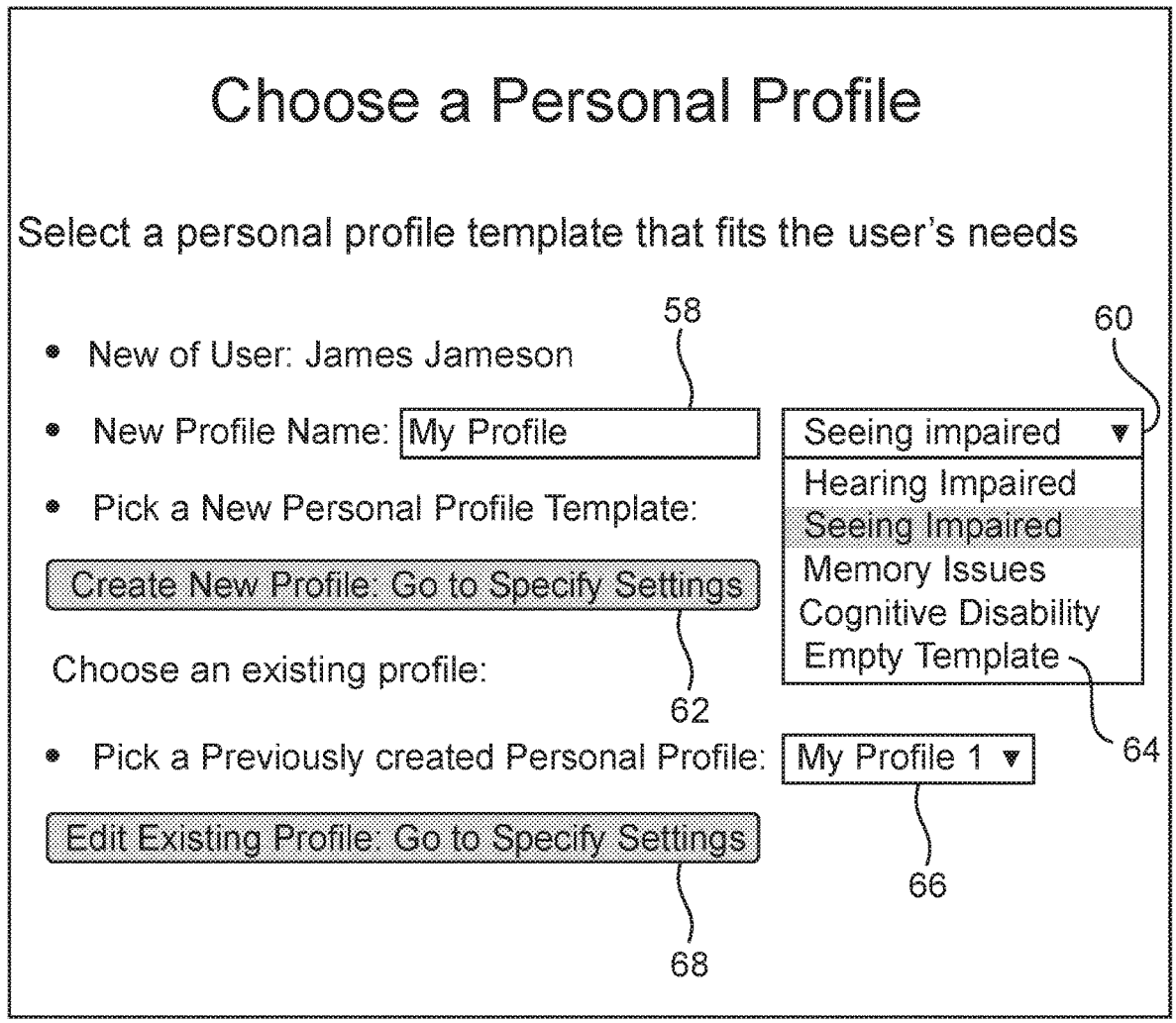

The browser then displays the "Choose a Personal Profile" page illustrated in FIG. 4B. In this embodiment, the personalization service generates an encrypted profile file to be used by an extension installed on the user's browser. The visitor may create a new profile for the user or may edit an existing profile, for example, to update it to accommodate changes in the user's condition or to try a different accommodation for an unchanged condition. In this embodiment, a default for the name of the user 10 is provided based on the visitor's sign in. Options may be coded for the visitor to request personalization for multiple users from a single account.

If the visitor opts to create a new profile, he enters a name for the new profile into the designated field 58. He then picks a template for preparing the personalization file by selecting choices from list presented on a pull-down menu 60. In this example, the visitor selected a personal profile template labeled "Seeing Impaired." The visitor then selects a button 62 labeled "Create a New Profile: Go to Specify Settings" to be prompted for more personalization data by the next web page.

The visitor had the option of selecting "Empty Template" 64, which is a more general template. After making this selection, the personalization service would then prompt the user for many more details than if he had selected one of the other templates.

If instead of creating a new profile the visitor opts to edit an existing profile, he must select the previously created personal profile from a pull-down menu 66. The visitor then selects a button 68 labeled "Edit Existing Profile: Go to Specify Settings" to be prompted for more personalization data.

As stated above, the visitor in this example opts to create a new profile and selects the button 62 labeled "Create a New Profile: Go to Specify Settings" after selecting a personal profile template. The personalization service then provides the web page illustrated in FIG. 4C, which confirms that the visitor selected the "Seeing Impaired" template. This template allows the user to select settings in pull-down menus 70, 72, 74, and 76 to choose the desired contrast level, text size, personal explanations to provide, and how the personal explanations are shown, respectively. For the last of the three settings, one option is "As Tooltip" and another (not shown) could be by added personal text in the page.

As an example of the last two settings in the "Specify Settings" page, the website visitor chooses as shown in FIG. 4C to provide a personal explanation to a homepage link on a content provider's website. That is, clicking on the homepage link brings a visitor to the website's homepage, but the user may be unable to see or to understand the content provider's label for the homepage link. Accordingly, it is then selected how the personal explanation of the homepage link is shown, which is as a tooltip. Then, when the user hovers his cursor over the web page link, a hover box opens displaying an image of a home and/or a text explanation that the link will lead the user to the website's home page.

With experience, some of the personalization service's account holders will gain an advanced proficiency with the personalization options. Such account holders, when reaching this step, may select the button 78 "Manually edit the profile file . . . " to specify additional details of the desired personalization.

After specifying the desired settings, the visitor may then select the button 80 "Save Changes." The visitor will then be prompted regarding details of where to send the encrypted profile file that the personalization engine will produce.

The disabilities discussed above and their accommodations are only a subset of the scope of what the present invention addresses. Another covered disability is dyscalculia, which causes severe difficulty in making mathematical calculations. The personalization can be color-coding, adding symbols, or adding explanatory text to help people with difficulty to understand numerical concepts to follow schedules and numerical information.

For example, consider a user accessing a website to obtain a bus schedule. Her computer determines her location, and the user specifies her desired destination. The website indicates when a particular bus will arrive to her location, but she cannot determine how much time she has at her disposal before the bus arrives. The output can be personalized to provide the text "Now (rush)," "Now," "Soon," "Soon (time for a cup of tea)," or "Soon (time for a short meal)" as is appropriate.

In another example, a user wants to know whether an item he is considering buying is permitted within his weekly budget. When viewing product information on his computer, a color coding of green for a good buy and red a bad buy guide him in making his decision whether to purchase the item. The analysis of whether the item should be purchased may be based on the whether the item fits within the user's overall budget, whether the item is expensive with respect to other items in the same category, for example, food, whether the item is expensive in comparison to similar foods, such as healthy vegetables. The analysis may be based on other useful guidelines.

In these examples, the user benefits from the additional information given in real time in a format that he can understand.

Supporting applications may be added to embodiments of the invention discussed above. For example, an initial setup application, for use by the user or her helper, could set a maximum on expenditures per week and/or per month, set a budget by category, such as supermarket, transport, clothes, education, bills, and miscellaneous, provide more detailed budget options for online shopping, set flags for unusual expenses must be approved by the customer and/or a customer-approved helper.

The setup application in the example can acquire the necessary data using four simple screens as follows.

Screen 1 asks how much can be spent per month on a particular credit or debit card. A check is made that the money is available every month.

Screen 2 provides basic categories of expenditures with a default suggested weekly budget based on a percentage of the total monthly budget. Additional options that may be provided "Add more" (increase the budget), "Add per month" (increase the monthly budget), and "Enable carry over" (apply to the next time period funds that were not spent in the last time period).

Screen 3 asks how the user would like to approve items that slightly exceed (such as by less than ten percent) the budget. The default approval method is through the application, but the user may opt to approve via telephone instead. Additional options are to notify a budget assisting application, such as an extension, require that the application approve such purchases, and to provide a time delay before the purchase is approved.

Screen 4 asks how the user would like to approve items that more significantly exceeds the budget (such as by more than ten percent). The application's default is by fingerprint and by notifying the budget assisting application. Additional options are to require a time delay and/or approval from the budget assisting application, to provide more notifications, and to warn the user when approaching the budget limit.

Additional transaction information provided may include the transactions that the user is conducting in real time. The application can identify an issue by directly comparing the budget data with the transaction data and then conclude whether a large amount has been spent in a category that suggests that safety mechanisms are needed.

Safety mechanisms may be implemented to require user approval in a way that works best for a particular user, such as via a conformation application, text, email, or phone conformation to the user and or caretaker, or any combination of the above. Safety measures may take the form of an application that provides the notification screen illustrated in FIG. 5.

In another embodiment, the system also uses a pattern analysis unit to determine whether unusual patterns exist. The system identifies at-risk patterns, such as travel tickets paid for by the customer but ticketed in the name of someone else (a sign that this may be a coerced "gift," which frequently indicates that a relative or caretaker is manipulating a vulnerable person) or two identical transactions made within a short period of time (a sign that a vendor may be exploiting a vulnerable person's forgetfulness and billing for an item for which he has already paid).

Safety mechanisms can be added for users with dyscalculia, and some of the safeguards can also be useful for users with dementia. For example, if based on previously-entered budget guidelines the personalized computer determines that an item considered for purchase is far outside budget allotments, the computer indicates such to the user and gives the user the options to cancel the sale or to wait a short period of time, such as an hour, to consider the purchase further. The personalized computer can also check for identical purchases made within a short period of time, such as buying an airline ticket twice, as a possible indication that the user only intended to make one purchase but forgot the first purchase and proceeded to make the purchase again.

Having thus described exemplary embodiments of the invention, it will be apparent that various alterations, modifications, and improvements will readily occur to those skilled in the art. For example, although the examples provided above of personalized output were visual, the invention applies equally to personalizing audio outputs. Alternations, modifications, and improvements of the disclosed invention, though not expressly described above, are nonetheless intended and implied to be within spirit and scope of the invention. Accordingly, the foregoing discussion is intended to be illustrative only; the invention is limited and defined only by the following claims and equivalents thereto.

I claim:

1. A method of enabling a client computer to personalize content for a user with a disability, the method comprising:
   receiving through a network data that specifies the personalization to accommodate the user having a particular disability;
   generating a personalization file based on the received data; and
   providing through the network the personalization file to the client computer;
   wherein the client computer uses the personalization file to personalize content to accommodate the user;
   wherein the client computer has no direct mapping between the data that specified the personalization and the personalization file, thereby reducing the ability to identify the user's disability from the personalization file; and
   wherein the personalization includes at least one of the following:
   providing content in simpler form; augmenting content with explanatory information to accommodate users with cognitive disabilities;
   providing warning information; and providing warning information based on budget constraints to accommodate people with learning and cognitive disabilities.

2. The method of claim 1 further described by at least one of the following:
   the data specifying the personalization is not stored on the client computer after the personalization file is provided;
   the data specifying the personalization is received from the client computer;
   a personalization engine residing on a server receives via the Internet the data specifying the personalization, and the personalization engine provides the personalization file to the client computer via the Internet;
   the content to be personalized is accessed by a browser residing on the client computer; and the personalization file is an executable script.

3. The method of claim 1, wherein the personalization file is an extension installed on the browser.

4. The method of claim 1, wherein the personalization file is an encrypted profile file used by an extension installed on the browser.

5. A personalization service server computer for enabling a client computer to personalize content for a user with a disability, the server computer comprising:
   a personalization engine that, when activated, accepts through a network data that specifies the personalization to accommodate the user having a particular disability;
   generates a personalization file based on the received data; and provides through the network the personalization file to the client computer;
   wherein the client computer uses the personalization file to personalize content to accommodate the user;
   wherein the client computer has no direct mapping between the data that specified the personalization and the personalization file, thereby reducing the ability to identify the user's disability from the personalization file; and
   wherein the personalization includes at least one of the following: providing content in simpler form;
   augmenting content with explanatory information to accommodate users with cognitive disabilities; providing warning information; and
   providing warning information based on budget constraints to accommodate people with learning and cognitive disabilities.

6. The server computer of claim 5 further described by at least one of the following:
   the data that specified the personalization is not stored on the client computer after the personalization file is provided;
   wherein the data specifying the personalization is received from the client computer;
   wherein the content to be personalized is accessed by a browser residing on the client computer;
   wherein the personalization file is an executable script;

wherein the personalization file is an extension installed on the browser; and wherein the personalization file is an encrypted profile file used by an extension installed on the browser.

7. The method of claim 1, wherein the personalization data is stored securely on a server hosting a personalization engine that generated the personalization file so that a second personalization file can be made generated based on said personalization data with modifications to accommodate an additional user scenario.

8. The method of claim 1, wherein the personalization includes changing the form of numeric representation to accommodate users with dyscalculia and/or cognitive disabilities.

9. The method of claim 1, wherein the personalization includes at least one of the following:

changing textual representation to another form to accommodate users with cognitive disabilities; providing content in simpler form;

augmenting content with explanatory information to accommodate users with cognitive disabilities; providing warning information;

providing warning information based on budget constraints to accommodate people with learning and cognitive disabilities; and adding symbols.

* * * * *